(12) United States Patent
Abe

(10) Patent No.: US 7,011,627 B2
(45) Date of Patent: Mar. 14, 2006

(54) FLEXIBLE TUBE FOR AN ENDOSCOPE AND ELECTRONIC ENDOSCOPE EQUIPPED WITH THE FLEXIBLE TUBE

(75) Inventor: Masanao Abe, Saitama (JP)

(73) Assignee: PENTAX Corporation, Tokyo (JP)

( * ) Notice: Subject to any disclaimer, the term of this patent is extended or adjusted under 35 U.S.C. 154(b) by 69 days.

(21) Appl. No.: 10/441,062

(22) Filed: May 20, 2003

(65) Prior Publication Data
US 2003/0220543 A1 Nov. 27, 2003

(30) Foreign Application Priority Data
May 21, 2002 (JP) .............................. 2002-146877

(51) Int. Cl.
*A61B 1/00* (2006.01)
(52) U.S. Cl. ...................................... 600/139; 600/140
(58) Field of Classification Search ................. 600/139
See application file for complete search history.

(56) References Cited

U.S. PATENT DOCUMENTS

| | | | | |
|---|---|---|---|---|
| 4,981,478 A | * | 1/1991 | Evard et al. ................. | 604/527 |
| 5,885,207 A | | 3/1999 | Iwasaka | |
| 6,197,014 B1 | * | 3/2001 | Samson et al. ............. | 604/524 |
| 6,458,075 B1 | | 10/2002 | Sugiyama et al. | |
| 6,503,193 B1 | | 1/2003 | Iwasaki et al. | |
| 6,520,214 B1 | | 2/2003 | Sugiyama et al. | |
| 6,540,669 B1 | * | 4/2003 | Abe et al. ................... | 600/140 |

FOREIGN PATENT DOCUMENTS

| | | |
|---|---|---|
| JP | 5-50287 | 7/1993 |
| JP | 2001070238 | 3/2001 |

* cited by examiner

*Primary Examiner*—Beverly M. Flanagan
*Assistant Examiner*—Matthew J Kasztejna
(74) *Attorney, Agent, or Firm*—Greenblum & Bernstein, P.L.C.

(57) ABSTRACT

An flexible tube for an endoscope having excellent resilience and durability is provided. The flexible tube for an endoscope includes a spiral coil formed by helically winding a band-shaped member, a reticular tube formed by braiding a plurality of fine wires and provided over the spiral coil, and a flexible outer cover provided over the reticular tube. The fine wires include at least one first fine wire having a coating layer mainly made from a resin material and at least one second fine wire having no such a coating layer, and the first fine wire is made more flexible than the second fine wire. The difference between the flexibilities of the first fine wire and the second fine wire can be obtained in such a way (method) that the first fine wire is made from a constituent material softer than a constituent material of the second fine wire, or that the diameter of the first fine wire is made to be smaller than the diameter of the second fine wire, or the like.

21 Claims, 5 Drawing Sheets

FLEXIBLE TUBE FOR AN ENDOSCOPE AND ELECTRONIC ENDOSCOPE EQUIPPED WITH THE FLEXIBLE TUBE

BACKGROUND OF THE INVENTION

1. Field of the Invention

This invention relates to a flexible tube for an endoscope and an endoscope equipped with the flexible tube.

2. Description of the Prior Art

Endoscopes for medial use or industrial use are equipped with flexible tubes (flexible tubes for endoscopes). Generally, the conventional flexible tubes for endoscopes have a structure which includes an elongated tubular core obtained by covering the outer periphery of aspiral coil with a reticular tube (braided member) and an outer cover formed of a synthetic resin or the like and provided over the outer periphery of the tubular core.

In endoscopic examination, the flexible tube for an endoscope is inserted along the body cavity to a deep part such as the stomach, duodenum, small intestine, and large intestine with being bent appropriately according to the shape of the path. In order to perform the inserting operation easily and reliably, it is necessary for the flexible tube that a push-in force applied to the proximal end (an end which is close to the operator) of the flexible tube is fully transmitted to its distal end. In other words, an flexible tube for an endoscope in which buckling is likely to occur has a poor operability. Here, "buckling" means a state that the push-in force applied at the proximal end of the flexible tube can not be fully transmitted to the distal end thereof because the push-in force is partially absorbed by a bent part in the flexible tube (where the buckling occurs). In order to avoid the occurrence of such buckling, it is necessary for a flexible tube for an endoscope to have sufficient flexibility so as to be able to withstand applied bending forces that would cause buckling. Further, the outer cover must be firmly attached or adhered to the tubular core since buckling is liable to occur at areas where the outer cover is peeled off from the tubular core.

Furthermore, in order to perform the inserting operation easily and reliably, It is also necessary for a flexible tube for an endoscope that when a rotational force (a twist) is applied to the proximal end thereof, the rotation is fully transmitted to the distal end thereof without being absorbed somewhere along the flexible tube. In other word, a flexible tube for an endoscope is also required to have satisfactory rotation followability at the distal end thereof for rotational force applied at the proximal end.

One example of such flexible tubes is disclosed in Japanese Examined Patent Publication No. Hei 5-50287, in which an outer cover of a flexible tube for an endoscope is constructed from a double layer structure comprised of an outer layer made of a material having good flexibility and an inner layer made of a material having good resiliency, thereby improving elasticity or resiliency of the flexible tube for an endoscope as a whole.

However, in the above-mentioned prior art, the adhesion (bonding strength) between the outer cover and the core has been left out of consideration. Therefore, in the flexible tube of the prior art, there is a case that the outer cover is peeled off from the core (that is, floating-up of the outer cover occurs) because of bending stress or twisting stress is exerted frequently at an area in the vicinity of a boundary surface between the outer cover and the core by repeatedly using the flexible tube, and thereby the resilience and the buckling withstanding property of the flexible tube are lowered. In other words, the prior art flexible tube involves a problem in its durability.

SUMMARY OF THE INVENTION

It is therefore an object of the present invention to provide a flexible tube for an endoscope in which peeling-off of the outer cover (that is, floating-up of the outer cover) is hard to occur so that the flexible tube has excellent resilience and durability.

In order to achieve the above object, the present invention is directed to a flexible tube for an endoscope which includes a spiral tube formed by helically winding a band-shaped member; a fine wire assembly constituted from a plurality of fine wires and provided over the spiral tube; and a flexible outer cover provided over the fine wire assembly, wherein the fine wires include at least one first fine wire having a coating layer mainly made from a resin material and at least one second fine wire having no such a coating layer, and the first fine wire is made more flexible than the second fine wire.

According to the flexible tube for an endoscope having the above-described structure, the adhesion between the fine wire assembly and the outer cover is improved to prevent the outer cover from been peeled off from the fine wire assembly in particular even in the case where the bending stress or twisting stress is applied repeatedly, thereby enabling to provided a flexible tube for an endoscope having excellent resilience and durability as well as an endoscope having the flexible tube.

In the present invention, the fine wire assembly is preferably constructed from a braid which is formed by braiding the first and second fine wires. By constructing the fine wire assembly from the braid, it is possible for the fine wire assembly to more effectively exhibit a function that relieves a locally exerted load.

In the present invention, it is preferred that the outer cover has a portion which is located adjacent to the fine wire assembly and is formed of a constituent material, and the resin material of the coating layer contains the constituent material of the portion of the outer cover. According to this structure, the adhesion between the fine wire assembly and the outer cover is further enhanced, so that the resilience and the durability of the flexible tube for an endoscope is further improved. In this structure, it is preferred that the resin material of the coating layer contains the constituent material of the portion of the outer cover in an amount of 5 to 8 wt % of the resin material of the coating layer. According to this structure, the adhesion between the fine wire assembly and the outer cover is still further enhanced, so that the resilience and the durability of the flexible tube for an endoscope is still further improved.

Further, in the present invention, it is preferred that the difference between the flexibilities of the first fine wire and the second fine wire is obtained by forming the first fine wire from a material softer than a material of the second fine wire. According to this structure, the difference between the flexibilities of the first fine wire and the second fine wire can be obtained relatively easily and reliably, and thus it is possible to manufacture the flexible tube for an endoscope easily.

Further, in the present invention, the difference between the flexibilities of the first fine wire and the second fine wire may be obtained by forming the first fine wire so as to have a diameter smaller than a diameter of the second fine wire. According to this structure, the difference between the flexibilities of the first fine wire and the second fine wire can also be obtained relatively easily and reliably, and thus it is also possible to manufacture the flexible tube for an endoscope easily.

Furthermore, in the present invention, the difference between the flexibilities of the first fine wire and the second fine wire may be obtained by changing the processing condition and/or heat treatment condition between the first and second fine wires. According to this structure, the difference between the flexibilities of the first fine wire and the second fine wire can also be obtained relatively easily and reliably, and thus it is also possible to manufacture the flexible tube for an endoscope easily.

In the present invention, it is also preferred that the ratio of the number of the first fine wires to the number of the second fine wires in the fine wire assembly lies within the range of 1:15 to 3:1. This makes It possible to secure the adhesion between the fine wire assembly and the outer cover sufficiently.

Further, it is also preferred that the constituent material of the coating layer has a melting point higher than a melting point of the constituent material of the outer cover. This makes it possible to further improve the resilience and the durability of the flexible tube for an endoscope. In this case, it is preferred that the difference between the melting point of the constituent material of the coating layer and the melting point of the constituent material of the portion of the outer cover lies within the range of 4 to 200° C. This makes it possible to still further improve the resilience and the durability of the flexible tube for an endoscope.

In the present invention, it is preferred that the constituent material of the outer cover contains a polyurethane based elastomer. This makes it possible to improve the flexibility of the flexible tube for an endoscope.

Further, it is also preferred that the constituent material of the coating layer contains a polyurethane based elastomer. This makes it possible to further improve the resilience and the durability of the flexible tube for an endoscope.

Furthermore, it is also preferred that the constituent material of the coating layer contains a polyamide based resin. This also makes it possible to further improve the resilience and the durability of the flexible tube for an endoscope.

Moreover, it is also preferred that the constituent material of the coating layer contains a fluoro based resin. This makes it possible to improve chemical resistance.

In the present invention, it is preferred that the average thickness of the coating layer lies within the range of 0.01 to 0.1 mm. This also makes it possible to further improve the resilience and the durability of the flexible tube for an endoscope.

Further, in the present invention, it is preferred that the average thickness of the outer cover lies within the range of 0.1 to 15 mm. This also makes it possible to further improve the resilience and the durability of the flexible tube for an endoscope.

Further, in the present invention, it is preferred that the outer cover is formed from a plurality of layers. This also makes it possible to further improve the resilience and the durability of the flexible tube for an endoscope.

Further, in the present invention, it is preferred that the outer cover is formed by an extrusion molding method. This also makes it possible to further improve the resilience and the durability of the flexible tube for an endoscope.

Another aspect of the present invention is directed to an endoscope equipped with the flexible tube for an endoscope described above.

These and other objects, structures and results of the present Invention will be apparent more clearly when the following detailed description of the preferred embodiments is considered taken in conjunction with the accompanying drawings.

DETAILED DESCRIPTION OF THE INVENTION

Hereinafter, a detailed description of the preferred embodiments of a flexible tube for an endoscope according to the present invention will be given with reference to the appended drawings.

Figure 1:
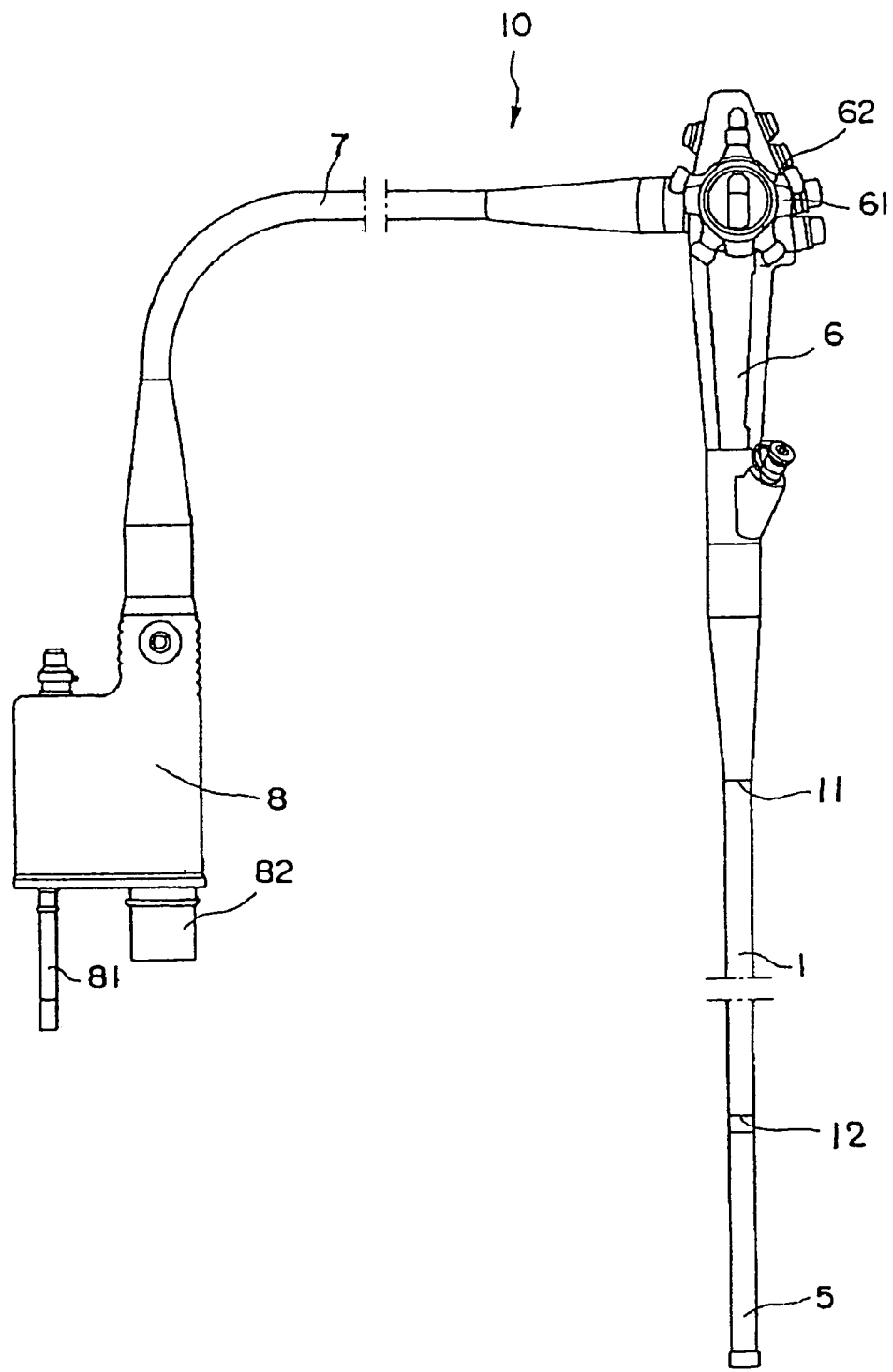
FIG. 1 is an overall view showing an electronic endoscope having a flexible tube for an endoscope constructed in accordance with the present invention.

FIG. 1 is an overall view showing an electronic endoscope having a flexible tube for an endoscope constructed in accordance with the present invention. In the following description, the upper side and the lower side in FIG. 1 will be referred to as "base or proximal end" and "tip or distal end," respectively.

As shown in FIG. 1, the electronic endoscope 10 includes an elongated flexible tube (insertion section) 1 to be inserted into a body cavity of a living body; a bendable tube 5 provided on the tip end 12 of the flexible tube 1; an operating section 6 provided on the base end 11 of the flexible tube 1, which is held by an operator during an endoscopic examination to manipulate the endoscope 10; a light guide flexible tube 7 connected at one end thereof to the operating section 6; and a light source plug section 8 provided on the other end of the light guide flexible tube 7 for connection with a light source device (not shown in the drawings).

The flexible tube 1 is used by being inserted into a body cavity (a lumen of a living body) such as a digestive tract. On one side surface of the operating section 6, there are provided operating knobs 61 and 62. When changing the direction of the bendable tube 5 during the endoscopic examination, the operator turns each of the operating knobs 61 and 62 to pull appropriately wires (not shown) arranged in the flexible tube 1. In this way, the bendable tube 5 is bent to a desired direction.

An Imaging element (CCD) not shown in the drawings is provided in the tip end portion of the bendable tube 5 to take observation images of an observation region inside the body cavity. Further, an image signal connector 82 is provided at the tip end portion of the light source plug section 8. The image signal connector 82 is connected to the light source device which is connected to a monitor (not shown in the drawing) via a cable.

Further, a light source connector 81 is provided at the tip end portion of the light source plug section 8 and this light source connector 81 is connected to a light source device (not shown in the drawing). Light emitted from the light source device passes through the light source connector 81 and a light guide (not shown in the drawings) comprised of an optical fiber bundle that runs inside the light source plug section 8, the light guide flexible tube 7, the operating section 6, the flexible tube 1 and the bendable tube 5, and then the light is irradiated from the tip end portion of the bendable tube 5 toward the observation region for illumination.

The reflected light from the observation region (which forms an image of the observation region) is received by the imaging element. Then, the imaging element outputs an image signal corresponding to the image formed on the imaging element by the reflected light.

The image signal is transmitted to the light source plug section 8 via an image signal cable (not shown in the drawing) which extends inside the bendable tube 5, the flexible tube 1, the operating section 6 and the light guide flexible tube 7.

Then, in the light source device, the image signal is subjected to predetermined processing (such as signal processing, image processing, and the like), and then the processed signal is sent to the monitor. In this way, an image (electronic image) taken by the imaging element is displayed on the screen of the monitor in the form of a motion picture.

In the above, the description was given for the case where the flexible tube for an endoscope according to the present invention is applied to an electronic endoscope (electronic type endoscope). However, it is to be noted that the flexible tube of this invention may also be applied to a flexible tube of an optical type endoscope.

Figure 2:
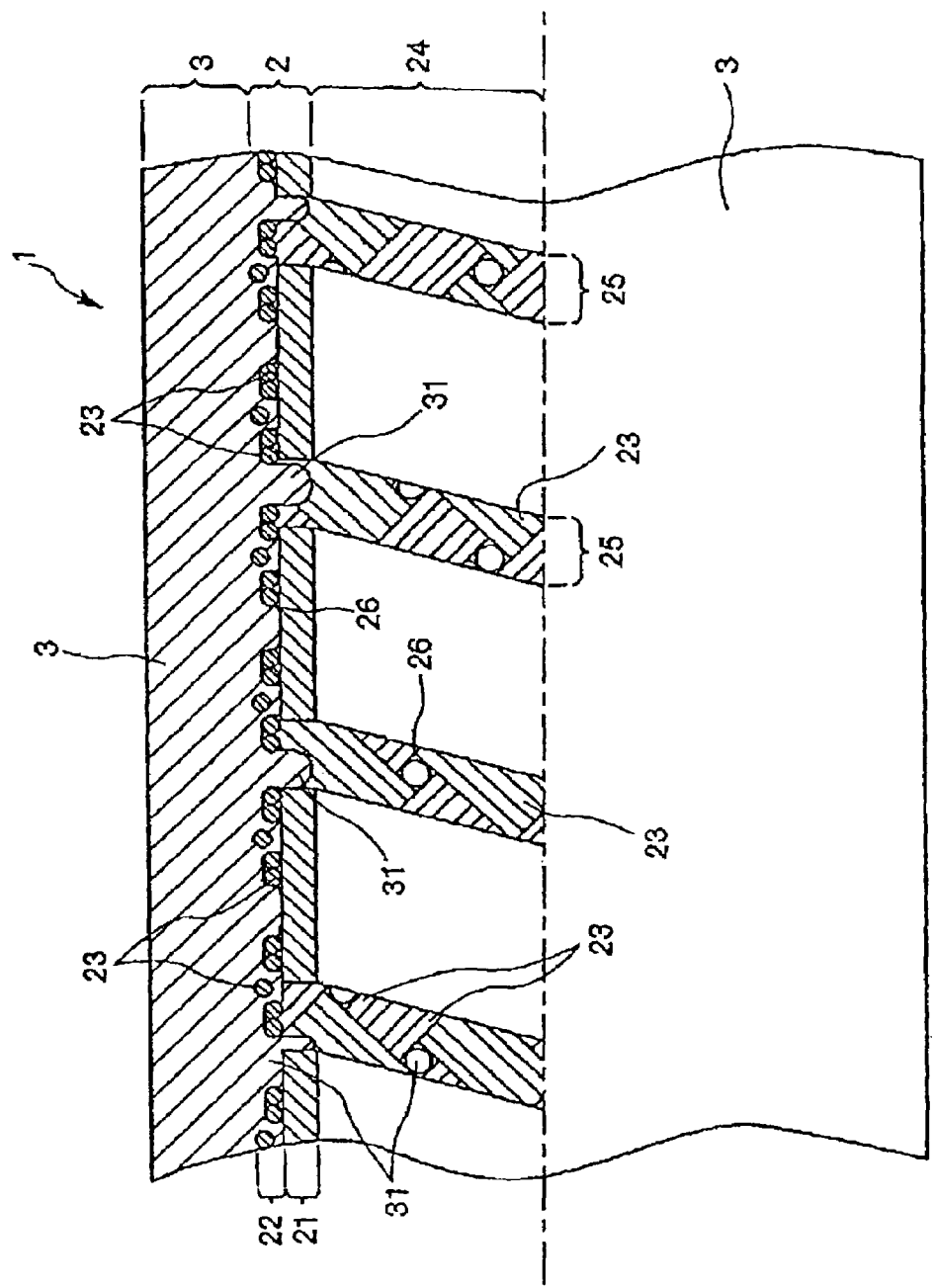
FIG. 2 is an enlarged partially cross-sectional view of a portion of a flexible tube for an endoscope of a first embodiment according to the present invention.

FIG. 2 is an enlarged partially cross-sectional view of a portion of a flexible tube for an endoscope of a first embodiment according to the present invention.

As shown in FIG. 2, the flexible tube 1 has a core body 2 and an outer cover 3 that covers the outer periphery of the core body 2. Further, inside the flexible tube 1, there is formed hollow spaces (lumens) 24 through which internal elements (such as optical fibers, cables, operation wires, tubular elements, and the like) can be passed.

The core body 2 is formed into an elongated tubular shape, and it is constructed from a spiral coil 21 and a reticular tube 22 which covers the outer periphery of the spiral coil 21. The core body 2 acts as a reinforcing member for reinforcing the flexible tube 1. By constructing the core body 2 from the coil 21 and the reticular tube 22 described above, it is possible to give the flexible tube 1 sufficient mechanical strength.

The spiral coil 21 is formed from a flat metal band. Specifically, this spiral coil 21 is formed by winding the metal band into a helical or spiral form so as to have a uniform diameter with a gap 25 between the adjacent windings. Preferred examples of materials which may be used for the metal band include stainless steel, copper alloys, and the like.

Figure 3:
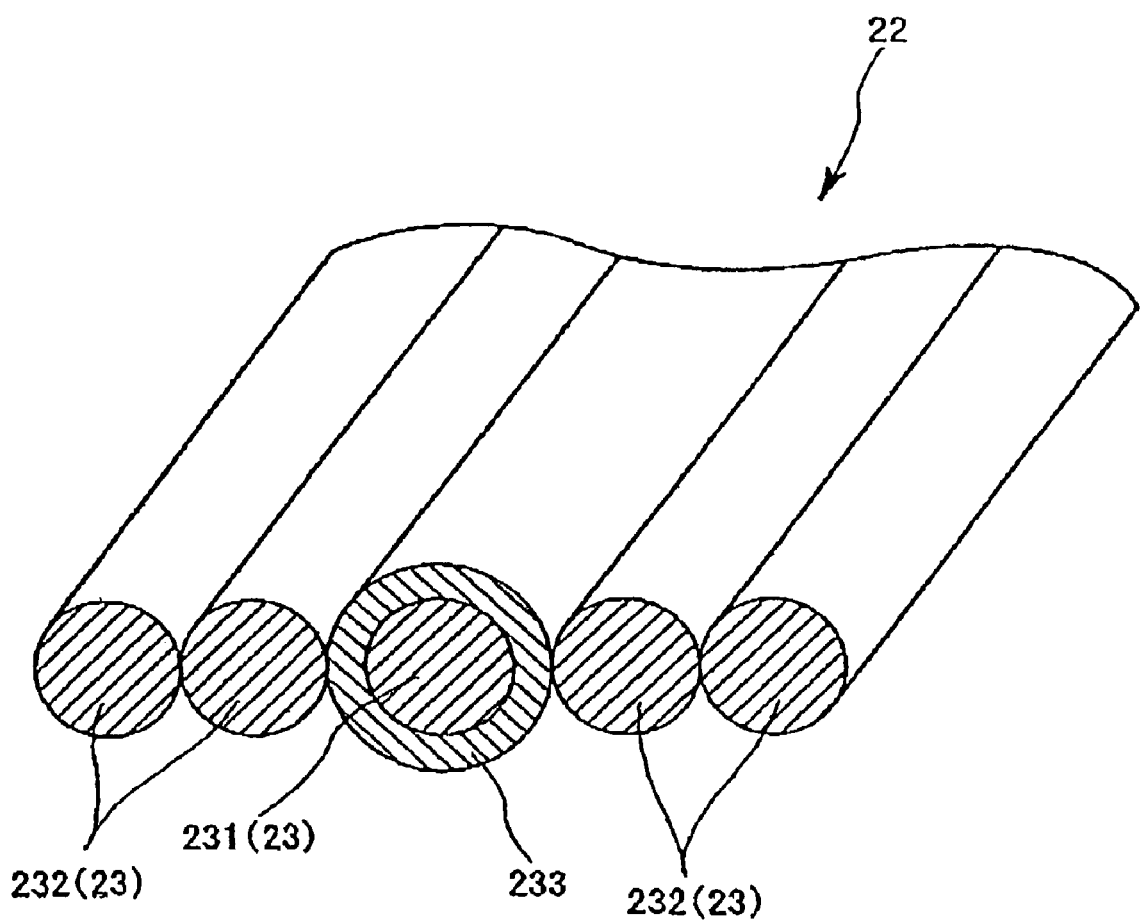
FIG. 3 is an enlarged cross sectional view of a thin wire assembly (a reticular tube) which is used in the flexible tube for an endoscope of the present invention.
Figure 4:
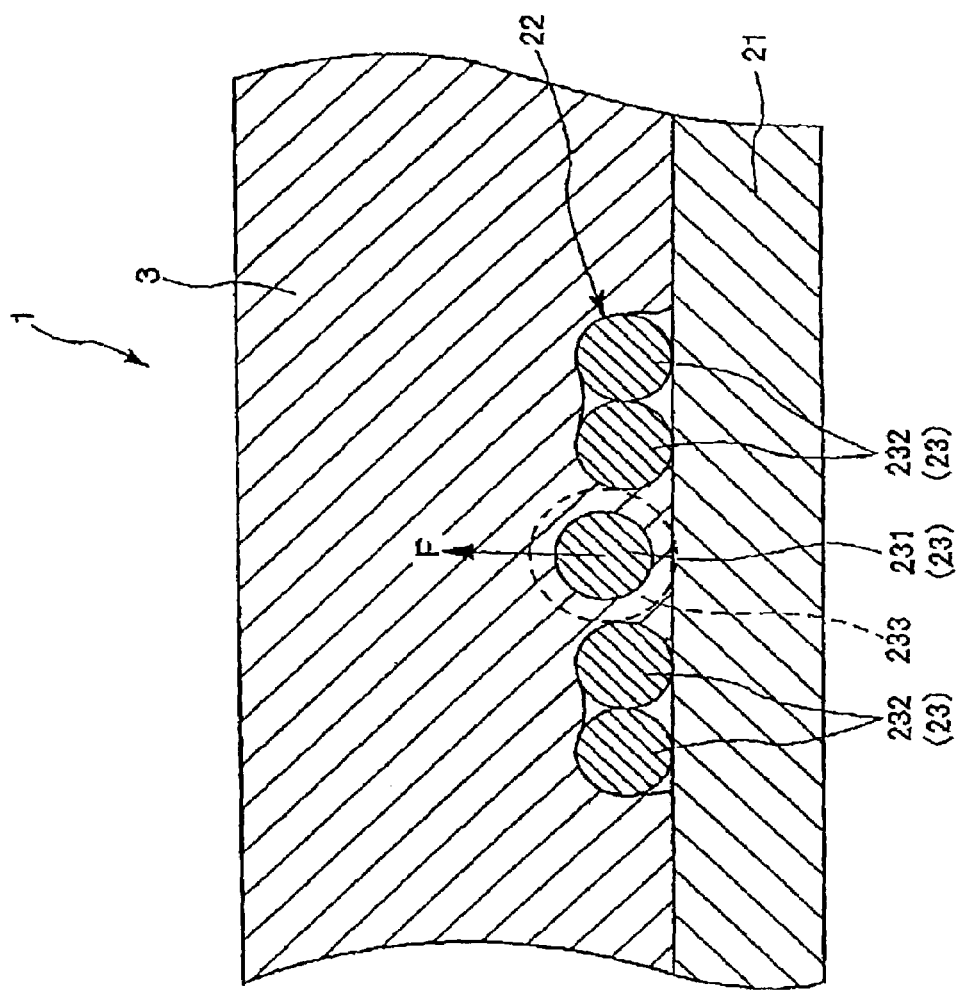
FIG. 4 is an enlarged cross sectional view which shows the structure of a portion in the vicinity of the reticular tube of the flexible tube shown in FIG. 2.

FIG. 3 is an enlarged cross-sectional view of a reticular tube (fine wire assembly) which is used for the flexible tube for an endoscope of the present invention. FIG. 4 is an enlarged cross sectional view which shows the structure of a portion in the vicinity of the reticular tube of the flexible tube shown in FIG. 2.

The reticular tube (braid) 22 is one example of the fine wire assembly comprised of a plurality of wires (including fine wires 231, 232), and in particular it is formed by braiding a plurality of fine wire bundles In which each bundle includes metals or nonmetal fine wires 23 arranged side by side into a tubular lattice structure (reticular tube). Properties and structural materials of each fine wire 23 will be described later in details.

As shown in FIG. 3, a coating layer (coating) 233 is formed over at least one of the fine wires 23 is formed with a coating layer 233 which covers the outer periphery of the fine wire, and other fine wires do not have such a coating layer 233. Hereinbelow, for the sake of clarity, the fine wire formed with the coating layer 233 is referred to as a fine wire (first fine wire) 231 and the fine with having no such a coating layer 233 is referred to as a fine wire (second fine wire) 232.

The properties (physical properties) of the fine wire 231 are different from those of the fine wire 232. Namely, the fine wire 231 is made more flexible than the fine wire 232. With this result, a stress applied to the fine wire 231 when a bending stress (which is mainly caused by a bend) or a twisting stress is exerted in the flexible tube 1 (in particular, a stress exerted in the direction shown by the arrow F in FIG. 4) is moderated (reduced) or absorbed by the surrounding region, so that followability of the fine wires 23 (in particular, followability to bend or twist) is improved. Consequently, peeling-off of the outer cover 3 from the reticular tube 22, namely peeling-off at a boundary area between the outer cover 3 and the melted coating layer 233 is prevented, and separation of the coating layer 233 from the fine wire 231 is also prevented.

Such differences in flexibility between the fine wire 231 and the fine wires 232 can be provided by the following methods (1) to (4), for example.

(1) The fine wire 231 is made from a constituent material softer than a constituent material of the fine wire 232.

As for the constituent materials of the fine wire 231 and the fine wires 232, various metallic materials such as iron alloy (e.g. stainless steel), copper alloy, nickel alloy (for example, Ni—Ti alloy), and non-metallic materials such as resins having a high melting point, carbon fibers, glass fibers, and the like can be mentioned.

Examples of stainless steel used for the metallic material include SUS201 (-W1, -W2, -W 1/2H), SUS302 (-WPA,-WPB), SUS303 (-W1, -W2), SUS303Se (-W1, -W2), SUS304 (-W1, -W2, -W 1/2H, -WPA, -WPB), SUS304L (-W1, -W2), SUS304N1 (-W1, -W2, -W 1/2H, -WPA, -WPB), SUS305 (-W1, -W2), SUS305J1 (-W1, -W2), SUS309S (-W1, -W2), SUS310S (-W1, -W2), SUS316(-W1, -W2, -W 1/2H, -WPA), SUS316L (-W1, -W2), SUS321 (-W1, -W2), SUS347 (-W1, -W2), SUSXM7 (-W1, -W2), SUS430 (-W2), SUS430F (-W2), SUS410 (-W2), SUS416 (-W2), SUS420J1 (-W2), SUS420J2 (-W2), SUS420F (-W2), SUS440C (-W2), and SUS631J1 (-WPC), and the like. Examples of the copper or copper alloy include C1100 (-O, -1/2H, -H), C1201 (-O, -1/2H, -H), C1220 (-O, -1/2H, -H), C2100 (-O, -1/2H, -H), C2200 (-O, -1/2H, -H), C2300 (-O, -1/2H, -H), C2400 (-O, -1/2H, -H), C2600 (-O, -1/8H, -1/4H, -1/2H, -3/4H, -H, -EH), C2700 (-O, -1/8H, -1/4H, -1/2H, -3/4H, -H, -EH), C2720 (-O, -1/8H, -1/4H, -1/2H, -3/4H, -H, -EH), C2800 (-O, -1/8H, -1/4H, -1/2H, -3/4H, -H), C3500 (-O, -1/2H, -H), C3501 (-O, -1/2H, -H), C3601 (-O, -1/2H, -H), C3602 (-F), C3603 (-O, -1/2H, -H), and C3604 (-F), and the like. Among these materials, an arbitral combination of one having a large breaking strength (N/mm$^2$) and the other having a small breaking strength (or a small elongation), or an arbitral combination of one having a large elongation (%) and the other having a small elongation is selected, and these metallic materials are used for the constituent materials of the fine wire 231 and the fine wires 232, respectively.

In this regard, it is to be noted that the physical properties of each of these materials such as breaking strength (N/mm$^2$) and elongation (%) are mentioned in JISG4309, JISG4314, JISH3250, JISH3260, and the like.

(2) The diameter of the fine wire 231 is made to be smaller than the diameter of the fine wire 232.

For example, if the fine wire 231 and the fine wire 232 are formed of the same material, the diameter of the fine wire 231 can be reduced to 20–95% of the diameter of the fine wire 232.

(3) The processing condition and/or the heat treatment condition is changed in each of the fine wire 231 and the fine wire 232.

Here, the processing condition means, for example, degree of processing from the raw material (degree of decrease of cross section or the like) in manufacturing the fine wires 231, 232. Further, heat treatment condition means, for example, heat history pattern, in particular cooling condition such as heating temperature or cooling rate (e.g. hardening and annealing). By selecting such processing condition and the heat treatment condition appropriately, or by selecting the combination of the processing condition and the heat treatment condition appropriately, it is possible to give different flexibilities to the fine wires.

(4) Any arbitral combination of two or three of the above-mentioned methods.

In this connection, however, please note that it goes without saying that the method for differentiating the flexibilities of the fine wire 231 and the fine wire 232 is not limited to the above-mentioned methods (1) to (4).

The ratio of the number of the fine wire 231 to the number of the fine wire 232 in the reticular tube 22 is not limited to any specific value, but preferably the ratio of the number of the fine wire 231 to the number of the fine wire 232 lies within the range of 1:15 to 3:1. If the ratio of the number of the fine wire 231 in the reticular tube 22 is too low, the total area (volume) of the coating layers 233 becomes small, thus resulting in a case that the adhesion strength between the outer cover 3 and the reticular tube 22 is lowered depending on other conditions. On the other hand, if the ratio of the number of the fine wire 231 in the reticular tube 22 is too high, further improvement of the adhesion strength can not be expected.

The coating layer 233 provided on the fine wire 231 is mainly constituted,from a resin material. In this regard, it is preferred that the coating layer is constituted from a material which contains the constituent material of the outer cover 3 (that is, the constituent material of at least a portion of the outer cover 3 facing the reticular tube 22 ) described later in detail. In this regard, it should be noted that the constituent material means the main material of the outer cover, and does not include additives and the like. By providing such a coating layer 233, it becomes possible to strongly adhere (fuse together) the coating layer 233 and the outer cover 3, as shown in FIG. 4. As a result, the adhesion strength (bonding strength) between the reticular tube 22 and the outer cover 3 is enhanced, so that the resilience and durability of the flexible tube 1 are improved.

Normally, the material used for the constituent material of the outer cover 3 is chosen in view of its cushioning ability (flexibility). Therefore, if the ratio of the constituent material of the outer cover 3 contained in the, constituent material of the coating layer 233 is too high, the coating layer 233 will have a high viscosity. As a result, when braiding the fine wire 231 covered with the coating layer 233, such braiding operation will become difficult due to the high viscosity, thus leading to the case that the reticular tube 22 has an uneven surface. On the other hand, if the ratio of the constituent material of the outer cover 3 contained in the constituent material of the coating layer 233 is too low, a sufficient adhesion (bonding strength) between the coating layer 233 and the outer cover 3 will not be obtained, which results in the case that the effect of the present invention is not sufficiently obtained. Accordingly, the ratio of the constituent material of the outer cover 3 contained in the constituent material of the coating layer 233 should preferably be in the range of 5–80 wt %, more preferably in the range of 7–60 wt %, and even more preferably in the range of 10–50 wt %.

The outer cover 3 described above is usually formed by extrusion molding the constituent material of the outer cover 3 over the outer periphery of the core body 2 (i.e., the outer periphery of the reticular tube 22). In the case where the outer cover 3 is formed in this manner, the constituent material of the outer cover 3 needs to be sufficiently melted or softened in order to accomplish a good coating that does not form any unevenness or roughness.

However, in the case where the outer cover 3 is formed using such a constituent material, there is a case that the following problem will arise. Namely, If the melting point of the constituent material of the coating layer 233 is below the melting point of the constituent material of the outer cover 3, there is a rtsk that the coating layer 233 is melted when the outer cover 3 is formed and thereby the adhesion of the fine wire 231 and the coating layer 233 is lowered. In order to avoid such an unfavorable situation, in the present invention, when the constituent material of the coating layer 233 has a melting point $T_1$ (° C.), and the constituent material of the outer cover 3 has a melting point $T_2$ (° C.), it is preferred that the relationship $T_1 > T_2$ needs to be satisfied. In this case, it is particularly preferred that the difference between the melting point ($T_1$) of the constituent material of the coating layer 233 and the melting point ($T_2$) of the constituent material of the outer cover 3 lies within the range of 4–200° C., and more preferably in the range of 4–70° C. If the melting points $T_1$ and $T_2$ satisfy this relationship, it is possible to obtain good adhesion between the fine wire 231 and the coating layer 233 as well as good adhesion between the reticular tube 22 and the outer cover 3.

In this connection, it is pref erred that the melting point $T_1$ of the constituent material of the coating layer 233 is in the range of 120–350° C., and more preferably in the range of 180–330° C., for example.

The constituent material of the coating layer 233 is not particularly limited to a specific material. For example, it is possible to use various resins (in particular, various resins having flexibility) such as polyvinyl chloride, polyolefin (e.g., polyethylene, polypropylene, ethylene-vinylacetate copolymer), polyamide, polyester (e.g., polyethylene terephthalate (PET), polybutylene terephthalate), polyurethane, polystyrene resin, fluoro-based resin (e.g., polytetrafluoroethylene, ethylene-tetrafluoroethylene copolymer), polyimide, and the like; and one of various elastomers such as polyurethane-based elastomer, polyester-based elastomer, polyolefin-based elastomer, polyamide-based elastomer, silicone rubber, latex rubber, and the like; and blended body, copolymer (including block copolymer) or polymer alloy each containing at least one of these elastomers as a main ingredient. In this case, a mixture of one or two or more kinds of these materials may be employed.

Among these materials, a material containing polyamide-based resin is particularly preferred. When such a material containing the polyamide-based resin is used as the constituent material of the coating layer 233, it is possible to obtain excellent adhesion between the coating layer 233 and the fine wire 231 as well as excellent adhesion between the coating layer 233 and the outer cover 3. This means that the adhesion between the reticular tube 22 and the outer cover 3 is also improved, and as a result, the flexible tube 1 will have excellent flexibility and durability.

Further, it is also preferred that the constituent material of the coating layer 233 contains polyurethane-based elastomer. When such a material containing the polyurethane-based elastomer is employed as the constituent material of the coating layer 233, it is also possible to obtain excellent adhesion between the outer cover 3 and the coating layer 233 and it is also possible for the flexible tube 1 to have excellent flexibility in the case where the constituent material of the outer cover 3 is polyurethane-based elastomer (in particular, a material containing polyurethane-based elastomer as its main ingredient).

Furthermore, it is also preferred that the constituent material of the coating layer 233 contains fluoro-based resin, in particular a fluoro-based resin having a melting point equal to or less than 300° C. By using such a constituent material, the coating layer 233 can have excellent adhesion with the fine wire 231 and the outer cover 3 Further, chemical resistance is also improved.

Examples of the fluoro-based resin having a melting point equal to or less than 300° C. include tetrafluoroethylene-hexafluoropropylene copolymer (FEP), tetrafluoroethylene-ethylene copolylmer (ETFE). polychlorotrifluoroethylene (PCTFE), chlorotrifluoroethylene-ethylene copolymer, polyvinylidene fluoride (PVDF), and polyvinyl fluoride (PVF) and the like, and polymer alloy (e.g. polymer blend or copolymer) containing two or more of the above-mentioned resins.

The average molecular weight (Mw) of the constituent material of the coating layer 233 is not particularly limited, but it should preferably lie within the range of 10000–8000000, and more preferably within the range of 15000–100000, for example.

When necessary, additives may be added to the constituent material of the coating layer 233.

Examples of the additives include plasticizer; various kinds of inorganic substances (inorganic filler); pigment; various kinds of stabilizers (such as antioxidant, photo stabilizer, antistatic agent, blocking inhibitor, lubricant); X-ray contrast medium, and the like.

The average thickness of the coating layer 233 is not particularly limited to a specific value, but it should preferably lie within the range of 0.01–0.1 mm, more preferably within the range of 0.02–0.08 mm, and even more preferably within the range 0.03–0.05 mm, for example. If the average thickness of the coating layer 233 is lower than the lower limit value, there is a possibility that the effect of the present invention is not sufficiently obtained. On the other hand, if the average thickness of the coating layer 233 exceeds the above upper limit, there is a case that the surface of the flexible tube 1 becomes rough or uneven, thus leading to poor appearance.

The reticular tube (braided member) 22 has many spaces due to the stitches of the braided fine wires 23. These spaces 26 become concave portions at the positions that overlap with the outer periphery of the coil 21 and become holes extending to the hollow spaces 24 at the positions which overlap with the gaps 25 of the coil 21. Therefore, a plurality of holes and concave portions are formed in the outer periphery of the core body 2.

Since the outer periphery of the core body 2 is covered with the flexible outer cover 3, a plurality of protruding portions (anchors) 31 which protrude toward the inside are formed on the inner peripheral surface of the outer cover 3 so as to be integral portions that extend into the spaces from the outer cover 3 Specifically, these protruding portions 31 extend into the plurality of holes and concave portions formed in the outer periphery of the core body 2. The tips of the protruding portions 31 that protrude into the concave portions are formed so as to reach the outer periphery of the coil 21. The protruding portions 31 that protrude into the holes are formed to be even longer so that the tips thereof can be extended into the gaps 25 of the coil 21.

As described above, the protruding portions 31 engage with the plurality of holes and concave portions formed in the outer periphery of the core body 2. Therefore, an anchoring effect will occur, and this will reliably secure the outer cover 3 to the core body 2. As a result, even in the case where the flexible tube 1 is bent, the outer cover 3 will maintain an adhering state with the core body 2, and will undergo large expansion and contraction to follow the bending of the core body 2. Further, the restoring force of the outer cover 3 undergoing such large expansion and contraction is strong enough to serve as a force for restoring the shape of the bent flexible tube 1. Accordingly, by adopting such structure as described above, the flexible tube 1 can have excellent resilience.

Further, due to the protruding portions 31 described above, the outer cover 3 is firmly adhered with the reticular tube 22, so that the outer cover 3 will be difficult to peel off from the reticular tube 22 even over repeated use. Accordingly, because the flexible tube 1 will maintain excellent resilience even after repeated use, the flexible tube 1 will have excellent durability.

Furthermore, the formation of the protruding portions 31 described above provides a synergistic effect in combination with the effect resulted from the provision of the coating layers 233 described above and the effect resulted from the difference in the flexibilities of the fine wire 231 and the fine wire 232, so that the flexible tube 1 can have especially excellent resilience and durability.

The melting point $T_2$ of the constituent material of the outer cover 3 varies depending on the type of constituent material to be used in the coating layer 233. Preferably, the melting point $T_2$ is in the range of 120–310° C., and more preferably in the range of 170–220° C.

The constituent material of the outer cover 3 is not particularly limited to a specific material. It is possible to use various resins having flexibility such as polyvinyl chloride, polyolefin (e.g., polyethylene, polypropylene, ethylene-vinylacetate copolymer), polyamide, polyester (e.g., polyethylene terephthalate (PET), polybutylene terephthalate), polyurethane, polystyrene resin, fluoro-based resin (e.g., polytetrafluoroethylene, ethylene-tetrafluoroethylene copolymer), polyimide, and the like; and various elastomers such as polyurethane-based elastomer, polyester-based elastomer, polyolefin-based elastomer, polyamide-based elastomer, silicone rubber, latex rubber, and the like; and blended body, copolymer (including block copolymer) or polymer alloy each containing at least one of these materials as a main ingredient. In this case, a mixture of one or two or more kinds of these materials may be employed. Among these materials, a material containing polyurethane-based elastomer is preferred, and a material containing polyurethane-based elastomer as its main ingredient is particularly preferred. By forming the outer cover 3 from such a material, it is possible to obtain a flexible tube 1 having excellent flexibility. Examples of the urethane-based elastomer include ether-based, ester-based, caprolactam-based, and polycarbonicacid-based, and the like.

The average molecular weight (Mw) of the constituent material of the outer cover 3 is also not particularly limited to a specific value. However, it is preferable that the average molecular weight is in the range of 10000–8000000, and more preferably in the range of 15000–100000.

When necessary, additives may be added to the constituent material of the outer cover 3.

Examples of the additives include plasticizer; various inorganic materials (inorganic filler); pigment; various kinds of stabilizers (such as antioxidant, photo stabilizer, antistatic agent, blocking inhibitor, lubricant); X-ray contrast medium, and the like.

A description of the constituent material of the outer cover 3 was given above. In this regard, it should be noted that the composition e.g. compounding ratio of the ingredients) of the constituent material of the outer cover 3 may be uniform throughout the entire of the outer cover 3, or may be varied at different portions of the outer cover 3. For example, the compounding ratio of the ingredients may be gradually changed in the thickness direction thereof (that is, graded materials may be used).

Further, it is preferred that the outer cover 3 (excluding those portions that have the protruding portions 31) has a substantially uniform thickness along the longitudinal direction thereof. This structure further improves the operability when the flexible insertion tube 1 is inserted into a body cavity, and thereby the burden placed on the patient can be further reduced.

In this regard, so long as the core body 2 and the instruments passed through the inside thereof are protected from body fluids and the like, and so long as the bendability of the flexible tube 1 is not impaired, there is no specific limitation on the average thickness of the outer cover 3 (excluding those portions that have the protruding portions 31), but normally the average thickness should preferably in the range of 0.01–1.5 mm, more preferably in the range of 0.05–1 mm, and even more preferably in the range of 0.1–0.8 mm.

An example of a manufacturing method for manufacturing the flexible insertion tube 1 will now be described.

First, the helical coil 21 and the reticular tube 22 are prepared.

The coil 21 is formed, for example, by preparing a metal plate, and then subjecting such a metal plate to a shearing process and then a winding process.

Further, the reticular tube 22 is formed by braiding fine wires 23 (231 and 232). In this regard, it is preferred that before the fine wires 23 are braided, the coating layer 233 is in advance formed on at least one of the fine wires 23.

The constituent material of the coating layer 233 is obtained, for example, by melting or softening each of the components described above, and then mixing and kneading such components together. In order to carry out such mixing and kneading of the melted or softened components, it is possible to use a kneading machine or the like such as a kneader, a kneading ruder, rollers, a continuous kneading extrusion machine or the like. In the case where such a kneading machine is used to knead the components together, the material will have a uniform mixture of the components.

As for the kneading temperature, there are no specific limits, but the temperature should preferably in the range of 140–360° C., more preferably in the range of 160–340° C., and even more preferably in the range of 180–320° C. In the case where each component is kneaded at a temperature within this range, it is possible to improve the uniformity of the components in the material.

However, in the case where the main component of the constituent material of the coating layer 233 is a rubber compound such as silicone rubber or the like, the heat generated during such kneading will degrade the plasticity of the constituent material of the coating layer 233. Accordingly, in this case, the kneading is preferably carried out at a temperature within the range of 10–70° C.

Then, the material kneaded in such a way is applied over the fine wire 23 by an extrusion molding method, molding method, dipping method, coating method or the like, and in this way it is possible to form the coating layer 233.

Next, the coil 21 and the reticular tube 22 obtained in this way are assembled to form the core body 2.

Then, the outer periphery of the core body 2 is covered with the outer cover 3 to form the flexible tube 1.

The constituent material of the outer cover 3 can be obtained, for example, by melting or softening each of the components described above, and then mixing and kneading such components together. In order to carry out such mixing and kneading of the melted or softened components, it is possible to use a kneading machine or the like such as a kneader, a kneading rooter, rollers, a continuous kneading extrusion machine or the like. In the case where such a kneading machine is used to knead the components together, the material will have a uniform mixture of the components.

As for the kneading temperature, there are no specific limitations, but the temperature should preferably in the range of 160–220° C., more preferably in the range of 180–210° C., and even more preferably in the range of 185–205° C. In the case where each component is kneaded at a temperature within this range, it is possible to improve the uniformity of the components in the material.

However, in the case where the main component of the constituent material of the outer cover 3 is a rubber compound such as silicone rubber or the like, the heat generated during such kneading will degrade the plasticity of the constituent material of the outer cover 3 Accordingly, in this case, the kneading is preferably carried out at a temperature within the range of 10–70° C.

Further, when the outer cover material kneaded in this way is applied over the core body 2 using an extrusion molding method, it is possible to manufacture the flexible tube 1 in a continuous manner.

Preferably, the temperature t of the outer cover material during the extrusion molding is equal to or greater than the melting point ($T_2$) of the constituent material of the outer cover 3, and equal to or less than the melting point ($T_1$) of the constituent material of the coating layer 233. In the case where the temperature t of the outer cover material during extrusion molding is within such temperature range (i.e., $T_2 \leq t < T_1$), the material can have excellent moldability and processability when being formed into the outer cover 3, and thereby the adhesion with the coating layer 233 is improved. Further, because the temperature t of the outer cover material is less than the melting point ($T_1$) of the constituent material of the coating layer 233, it is possible to prevent the coating layer 233 from being melted during the extrusion molding process to lower the adhesion between the fine wire 231 and the coating layer 233. Consequently, the adhesion between the reticular tube 22 and the outer cover 3 is improved, and this gives the flexible tube 1 excellent resilience and durability.

Figure 5:
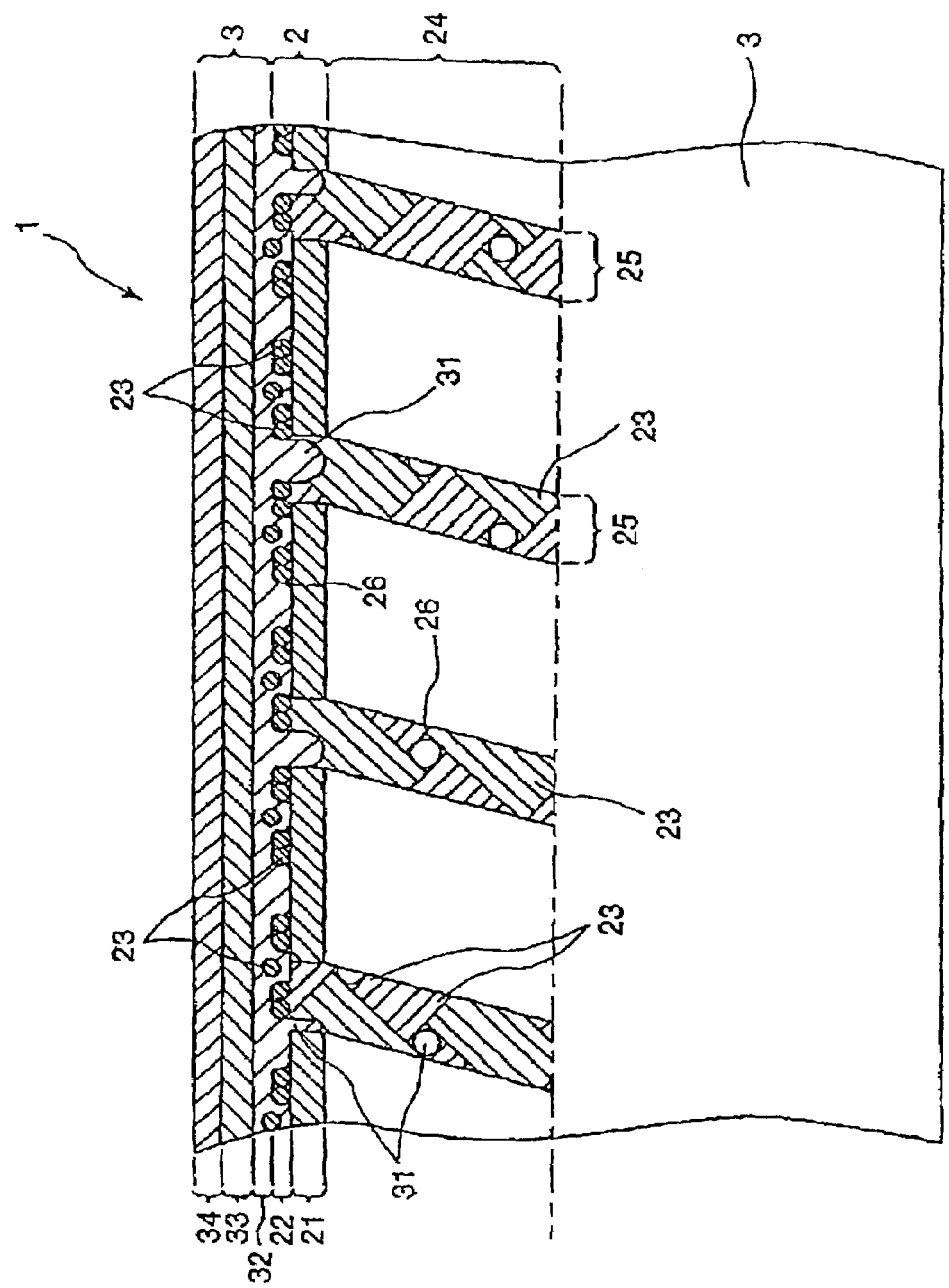
FIG. 5 is a partially cross-sectional view of a portion of a flexible tube for an endoscope of a second embodiment according to the present invention.

Next, FIG. 5 is a partially cross-sectional view of a portion of a flexible tube for an endoscope of a second embodiment according to the present invention. In this regard, the description given below for the flexible tube 1 shown in FIG. 5 will focus on elements that are different from those described above in the first embodiment, and therefore a description of the same elements is omitted.

In the flexible tube 1 of the second embodiment, the outer cover 3 is formed into a laminated structure which includes an inner layer 32, an intermediate layer 33 and an outer layer 34.

As described below, in this outer cover 3, one of the inner layer 32, the intermediate layer 33 and the outer layer 34 is made of a material having different physical and chemical properties (referred to collectively as the "material properties") than any one of the other layers. Examples of physical properties include stiffness (flexibility), hardness, elongation percentage, tensile strength, shear strength, flexural elasticity, bending strength and the like, and examples of chemical properties include chemical resistance, weather resistance and the like. In this regard, it should be noted that the present invention is not limited to these examples, and it is of course possible to include any other material properties.

The inner layer 32 is formed at the innermost peripheral side of the outer cover 3 so as to make contact with the core body 2. Accordingly, the constituent material of the inner layer 32 is preferably chosen to have excellent adhesion with the core body 2 (in particular, the coating layer 233). Further, the inner layer 32 is preferably formed of a material suited for forming protruding portions 31 having appropriate size (length), shape and number. By forming the inner layer 32 with such a material, it is possible to control the resilience and durability of the flexible tube 1.

Further, the Inner layer 32 is preferably formed of the same material used as the constituent material of the outer cover 3 of the first embodiment described above.

The average thickness of the inner layer 32 (excluding those portions that have the protruding portions 31 ) is not particularly limited to a specific value, but it should preferably be in the range of 0.03–0.8 mm, and more preferably in the range of 0.03–0.4 mm.

The intermediate layer 33 is formed over the outer peripheral surface of the inner layer 32. The intermediate layer 33 is preferably formed as a layer having better elasticity or resilience than the outer layer 34 described below. According to this structure, the intermediate layer 33 will function as a cushioning layer between the inner layer 32 and the outer layer 34. Further, the intermediate layer 33 is preferably formed as a layer having better flexibility than the inner layer 32.

The cushioning function of the intermediate layer 33 will now be described in detail. Namely, when the flexible tube 1 is bent, the deformed intermediate layer 33 generate is a strong restoring force because of the high resilience of the intermediate layer 33. Then, since the intermediate layer 33 is arranged between the outer layer 34 and the inner layer 32 both having relatively high hardness, the restoring force of the intermediate layer 33 is transmitted efficiently to the inner layer 32 and the outer layer 34, respectively. As a result, almost all of the restoring force of the intermediate layer 33 functions as a force for restoring the bent flexible tube 1. Accordingly, by constructing the outer cover 3 with the laminated structure described above, it is possible to obtain a flexible tube having excellent resilience.

The constituent material of the intermediate layer 33 is not particularly limited to a specific material. It is possible to use various resins having flexibility such as polyvinyl chloride, polyolefin (eg, polyethylene, polypropylene, ethylene-vinylacetate copolymer), polyamide, polyester (e.g., polyethylene terephthalate (PET), polybutylene terephthalate), polyurethane, polystyrene resin, fluoro-based resin (e.g., polytetrafluoroethylene, ethylene-tetrafluoroethylene copolymer), polyimide, and the like; and various elastomers such as polyurethane-based elastomer, polyester-based elastomer, polyolefin-based elastomer, polyamide-based elastomer, silicone rubber, latex rubber, and the like: and blended body, copolymer(including block copolymer) or polymer alloy each containing at least one of these materials as a main ingredient. In this case, a mixture of one or two or more kinds of these materials may be employed.

Among these materials, low hardness polyurethane-based elastomer, polyolefin-based elastomer, and polyester-based elastomer are particularly preferred because they have excellent resilience.

The average thickness of the intermediate layer 33 is not particularly limited, but it should preferably be in the range of 0.02–0.8 mm, and preferably in range of 0.02–0.4 mm.

The outer layer 34 is formed at the outermost peripheral side of the outer cover 3.

The outer layer 34 is preferably formed of a material having chemical resistance. By forming the outer layer from such a material, the outer cover 3 will suffer very little degradation even over repeated cleaning and sterilization. As a result, there is less possibility that the outer cover 3 is hardened to reduce its flexibility or that the outer cover 3 is peeled off from the reticular tube 22 due to occurrence of cracking and the like.

The constituent material of the outer layer 34 is not particularly limited. It is possible to use various resins having flexibility such as polyvinyl chloride, polyolefin (e.g. polyethylene, polypropylene, ethylene-vinylacetate copolymer), polyamide, polyester (e.g., polyethylene terephthalate (PET), polybutylene terephthalate), polyurethane, polystyrene resin, fluoro-based resin (e.g., polytetrafluoroethylene, ethylene-tetrafluoroethylene copolymer), polyimide, and the like; and various elastomers such as polyurethane-based elastomer, polyester-based elastomer, polyolefln-based elastomer, polyamide-based elastomer, silicone rubber, latex rubber, and the like; and blended body, copolymer (including block copolymer) or polymer alloy each having at least one of these materials as a main ingredient. In this case, a mixture of one or two or more kinds of these materials may be employed.

Among these materials, polyolefin such as ethylene-vinylacetate copolymer, fluoro-based resin such as polytetrafluoroethylene, ethylene-tetrafluoroethylene copolymer and the like, polyester-based elastomer, polyolefin-based elastomer, fluorine-based elastomer, and silicone rubber are particularly preferred because they have excellent chemical resistance.

The average thickness of the outer layer 34 is not particularly limited, but it should preferably be in the range of 0.05–0.8 mm, and more preferably in the range of 0.05–0.4 mm.

Further, It should be noted that the laminated structure formed by laminating the plurality of layers described above may be provided for the entire length of the outer cover 3 or for at least a part thereof.

By constructing the outer cover 3 from the laminated structure having the plurality of layers as described above it is possible to enjoy the advantages of the respective materials used in each layer. In this embodiment, because the outer cover 3 is constructed from the outer layer 34 having excellent chemical resistance the intermediate layer 33 having excellent resilience, and the inner layer 32 having excellent adhesion with the core body 2, all of the advantages resulted from these properties are enjoyed in the outer cover 3.

This type of flexible tube can be manufactured in the same manner as was described above for the first embodiment. In particular, in the case where an extrusion molding machine equipped with a plurality of extrusion openings is used, each of the inner layer, intermediate layer and outer layer is respectively extruded through such extrusion openings at the same time, and by covering the core body with such a laminated body, it is possible to continuously manufacture an outer cover having the laminated structure. Further, by adjusting the pulling speed of the core body and the discharge quantity of the constituent material of each layer extruded through each extrusion opening, it is possible to control the thickness of each layer.

In the foregoing, the description was made with regard to the preferred embodiments of the present invention. However, the present invention is not limited to these specific embodiments described above.

For example, in the second embodiment, instead of the three layered structure including the inner layer 32, the intermediate layer 33 and the outer layer 34, the outer cover 3 can be constructed from just two layers (e.g., the intermediate layer 33 can be omitted, and just the inner layer 32 and the outer layer 34 can be used), or the outer cover 3 can be constructed from four or more layers.

Further, as an alternative method of manufacturing the flexible tube for an endoscope, the following method may be employed. That is, first, the outer cover 3 is formed as a continuous elongated body, and then the core body 2 is inserted into this outer cover 3, whereafter a heating process or the like is carried out to bond the outer cover 3 to the core body 2.

Furthermore, the flexible tube for an endoscope of the present invention can also be applied to flexible connection tubes and the like connected to a light source device.

Moreover, the flexible tube for an endoscope of the present invention can also be applied to an optical endoscope besides an electronic endoscope, and it can be applied to not only an endoscope for medical use but also an endoscope for industrial use.

EXAMPLES

Next, specific examples of the present invention will be described below
1. Preparation of Flexible Tube for Endoscope Example 1

First, a spiral coil 21 having an outer diameter of 9.9 mm and an inner diameter of 9.6 mm was prepared by winding a band-shaped stainless steel member having a width of 3 mm.

Next, a stainless steel fine wire (made of SUS304-W1) having a diameter of 0.1 mm and a stainless steel fine wire (made of SUS304-w2) having a diameter of 0.1 mm were prepared. Then, the former wire was given a coating layer along the entire length thereof by an extrusion molding method. As the constituent material of the coating layer, a mixture containing 35 wt % of polyurethane-based elastomer (manufactured and sold by DAINIPPON INK AND CHEMICALS Inc. with the product name of "PANDEX" and the product code of T-1180) and 65 wt % of polyamide-based resin (manufactured and sold by Mitsubishi Engineering-Plastics Corporation with the product name of "NOVA-MID" and the product code of 1010C) was employed. The mixture had a melting point $T_1$ of 214° C. The average thickness of the coating layer was 0.05 mm.

A plurality of bundles each having seven fine wires were prepared. Each bundle was comprised of a fine wire (first fine wire) which was given the coating layer thereon and six fine wires (second fine wire) having no coating layer. These bundles were braided to obtain a reticular tube (the ratio of the number of the first wire to the number of the second wire was 1:6).

The coil was covered with the reticular tube obtained in this way to form a core body.

Next, the periphery of this core body was covered with an outer cover (having a melting point $T_2$ of 170° C.) made of polyurethane-based elastomer (manufactured and sold by DAINIPPON INK AND CHEMICALS Inc. with the product name of "PANDEX" and the product code of T-1180) by using the extrusion molding method to obtain a flexible tube for an endoscope with a length of 1.5 m. The temperature (t) of the outer cover material during extrusion molding was 200° C. Further, the average thickness of the outer cover of the flexible tube for an endoscope obtained in this way was 0.3 mm.

Example 2

A flexible tube for an endoscope was prepared in the same manner as in Example 1 except that a stainless steel fine wire (made of SUS304-W1) having a diameter of 0.1 mm was used for a fine wire having a coating layer (first fine wire) and a stainless steel fine wire (made of SUS304-WPB) having a diameter of 0.1 mm was used for a fine wire having no coating layer (second fine wire), to form a reticular tube.

Example 3

A flexible tube for an endoscope was prepared in the same manner as in Example 1 except that a copper alloy fine wire (made of C2800 1/2H) having a diameter of 0.1 mm was used for a fine wire having a coating layer (first fine wire) and a stainless steel fine wire (made of SUS304-WPB) having a diameter of 0.1 mm was used for a fine wire having no coating layer (second fine wire), to form a reticular tube.

Example 4

A flexible tube for an endoscope was prepared in the same manner as In Example 1 except that a stainless steel fine wire (made of SUS304-W1) having a diameter of 0.1 mm was used for a fine wire having a coating layer (first fine wire) and a stainless steel fine wire (made of SUS304-W1) having a diameter of 0.1 mm was used for a fine wire having no coating layer (second fine wire), to form a reticular tube, and that the average thickness of the coating layer was 0.06 mm Example 5

A flexible tube for an endoscope was prepared in the same manner as in Example 4 except that a stainless steel fine wire (made of SUS304-W1) having a diameter of 0.08 mm was used for a first fine wire which was annealed at a temperature of 900° C. to increase flexibility.

Example 6

A flexible tube for an endoscope was prepared in the same manner as in Example 1 excepting the following points.

As for the constituent material of the coating layer of the first fine wire, a mixture of 60 wt % of polyvinylidene fluoride (PVDF) (manufactured and sold by DAIKIN INDUSTRIES LTD. with the product name of "NEOFRON VDF") and 40 wt % of polychlorotrifluoroethylene (of which melting point was 192° C.) was used. The coating layer was formed by an extrusion molding method with the material temperature of 215° C. so as to have the average thickness of 0.04 mm.

Further, as for the constituent material of the outer cover, polyvinylidene fluoride (PVDF) (manufactured and sold by DAIKIN INDUSTRIES LTD. with the product name of "NEOFRON VDF", and having a melting point of 174° C.) was used. The outer cover was used by an extrusion molding method with the material temperature of 188° C. so as to have the average thickness of 0.4 mm.

Example 7

A flexible tube for an endoscope was prepared in the same manner as in Example 2 excepting that the coating layer and the outer cover were manufactured in the same manners as those of Example 6.

Example 8

A flexible tube for an endoscope was prepared in the same manner as in Example 3 excepting that the coating layer and the outer cover were manufactured in the same manners as those of Example 6.

Example 9

A flexible tube for an endoscope was prepared in the same manner as in Example 4 excepting that the coating layer and the outer cover were manufactured in the same manners as those of Example 6.

Example 10

A flexible tube for an endoscope was prepared in the same manner as in Example 5 excepting that the coating layer and the outer cover were manufactured in the same manners as those of Example 6.

Example 11

A flexible tube for an endoscope was prepared in the same manner as in Example 1 excepting that an outer cover provided over the core body was formed into a laminate structure including an inner layer, an intermediate layer and outer layer.

The outer cover having such a laminate structure was manufactured using an extrusion molding machine provided with three extrusion openings. Namely, the outer cover having the laminate structure was continuously manufactured by extruding the materials of the inner layer, the intermediate layer and the outer layer simultaneously so as to cover the core body.

Further, as for the constituent materials of each of these inner, intermediate and outer layers, polyurethane-based elastomer (manufactured and sold by DAINIPPON INK AND CHEMICALS Inc. with the product name of "PANDEX" and the product code of T-1180), polyurethane-based elastomer (manufactured and sold by DAINIPPON INK AND CHEMICALS Inc. with the product name of "PANDEX" and the product code of T-1498), and polyurethane-based elastomer (manufactured and sold by DAINIPPON INK AND CHEMICALS Inc. with the product name of "PANDEX" and the product code of T-1495) were used, respectively.

Furthermore, the average thickness of each of these inner, intermediate and outer layers were 0.05 mm, 0.1 mm and 0.1 mm, respectively.

Example 12

A flexible tube for an endoscope is prepared in the same manner as in Example 2 excepting that an outer cover was manufactured in the same manner as Example 11.

Example 13

A flexible tube for an endoscope is prepared in the same manner as in Example 4 excepting that an outer cover was manufactured in the same manner as Example 11.

Example 14

A flexible tube for an endoscope is prepared in the same manner as in Example 6 excepting that an outer cover was manufactured in the same manner as Example 11 in which the constituent material of the inner layer was changed to polyvinylidene fluoride (PVDF) (manufactured and sold by DAIKIN INDUSTRIES LTD. with the product name of "NEOFRON VDF", and having a melting point of 174° C.).

Example 15

A flexible tube for an endoscope was prepared in the same manner as in Example 11 excepting that a reticular tube was manufactured by braiding bundles of fine wires in which each bundle is comprised from four fine wires including one first wire and three second wires (the ratio of the number of the first fine wire to the number of the second fine wire was 1:3).

Example 16

A flexible tube for an endoscope was prepared in the same manner as in Example 14 excepting that a reticular tube was manufactured by braiding bundles of fine wires in which each bundle is comprised from five fine wires including two first wires (a diameter of which was 0.09 mm) and three second wires which were arranged alternately (the ratio of the number of the first fine wire to the number of the second fine wire was 2:3).

Comparative Example 1

A flexible tube for an endoscope was prepared in the same manner as in Example 1 except that no coated layer was formed on the fine wires.

Comparative Example 2

A flexible tube for an endoscope was prepared in the same manner as in Example 1 except that all the fine wires were manufactured from the same stainless steel fine wire (made from SUS304-W1) having a diameter of 0.1 mm.

Comparative Example 3

A flexible tube for an endoscope was prepared in the same manner as in Example 6 except that all the fine wires were manufactured from the same stainless steel fine wire (made from SUS304-W1) having a diameter of 0.1 mm.

2. Evaluation of Properties of the Flexible Tubes

<2.1> Resilience Test

A resilience test was conducted on each of the flexible tubes of Examples 1–16 and Comparative Examples 1–3.

In this resilience test, both ends of each of the flexible tubes were supported and then it was bend at 90°, and then the resilience at such time was evaluated according to the four ranking is given below.

A: Extremely good resilience; most suitable for use as a flexible tube for an endoscope B: Good resilience; suitable for use as a flexible tube for an endoscope C: Slightly poor resilience; questionable in suitability for use as a flexible tube for an endoscope after such repeated bending operation with the resilience before such repeated bending operation to evaluate the loss of resilience according to the four rankings given below. In this regard, it is to be noted that the loss of resilience is considered to be resulted from peeling off of the internal portion of the outer cover (i.e., the outer cover is peeled off from the core body). Accordingly, the flexible tubes that can maintain their resilience will have excellent durability.

A: Virtually no change in resilience; extremely good durability

B: Slight loss of resilience; good durability

C: Noticeable loss of resilience; questionable in its durability

D: Significant loss of resilience; degradation was confirmed at various positions The results of the durability test are also shown in the following Tables 1 and 2.

TABLE 1

|  | First Fine Wire | | Second Fine Wire | | | | | |
|---|---|---|---|---|---|---|---|---|
|  | Material | Diameter (mm) | Material | Diameter (mm) | Constituent Material of Coating Layer | Constituent Material of Outer Cover | Resilience Test | Durability Test |
| Example 1 | SUS304-W1 | 0.1 | SUS304-W2 | 0.1 | PU-based Elastomer + PA | PU-based Elastomer | B | B |
| Example 2 | SUS304-W1 | 0.1 | SUS304-WPB | 0.1 | PU-based Elastomer + PA | PU-based Elastomer | A | A |
| Example 3 | C2800 1/2H | 0.1 | SUS304-WPB | 0.1 | PU-based Elsstomer + PA | PU-based Elastomer | A | A |
| Exampre 4 | SUS304-W1 | 0.08 | SUS304-W1 | 0.1 | PU-based Elastomer + PA | PU-based Elastomer | B | A |
| Example 5 | SUS304-W1 Annealed | 0.08 | SUS304-W1 | 0.1 | PU-based Elastomer + PA | PU-based Elastomer | B | A |
| Example 6 | SUS304-W1 | 0.1 | SUS304-W2 | 0.1 | PVDF + PCTFE | PVDF | B | B |
| Example 7 | SUS304-W1 | 0.1 | SUS304-WPB | 0.1 | PVDF + PCTFE | PVDF | B | A |
| Example 8 | C2800 1/2H | 0.1 | SUS304-WPB | 0.1 | PVDF + PCTFE | PVDF | B | A |
| Example 9 | SUS304-W1 | 0.08 | SUS304-W1 | 0.1 | PVDF + PCTFE | PVDF | B | A |
| Example 10 | SUS304-W1 Annealed | 0.08 | SUS304-W1 | 0.1 | PVDF + PCTFE | PVDF | B | A |

TABLE 2

|  | First Fine Wire | | Second Fine Wire | | | | | |
|---|---|---|---|---|---|---|---|---|
|  | Material | Diameter (mm) | Material | Diameter (mm) | Constituent Material of Coating Layer | Constituent Material of Outer Cover | Resilience Test | Durability Test |
| Example 11 | SUS304-W1 | 0.1 | SUS304-W2 | 0.1 | PU-based Elastomer + PA | Inner Layer: PU-based Elastomer | B | B |
| Example 12 | SUS304-W1 | 0.1 | SUS304-WPB | 0.1 | PU-based Elastomer + PA | Inner Layer: PU-based Elastomer | A | A |
| Example 13 | SUS304-W1 | 0.08 | SUS304-W1 | 0.1 | PU-based Elsstomer + PA | Inner Layer: PU-based Elastomer | B | A |
| Exampre 14 | SUS304-W1 | 0.1 | SUS304-W2 | 0.1 | PVDF + PCTFE | Inner Layer: PVDF | B | B |
| Example 15 | SUS304-W1 | 0.1 | SUS304-W2 | 0.1 | PU-based Elastomer + PA | Inner Layer: PU-based Elastomer | B | A |
| Example 16 | SUS304-W1 | 0.09 | SUS304-W2 | 0.1 | PVDF + PCTFE | Inner Layer: PVDF | B | A |
| Comp. Ex. 1 | SUS304-W1 | 0.1 | SUS304-W2 | 0.1 | No Coating Layer | PU-based Elastomer | B | D |
| Comp. Ex. 2 | SUS304-W1 | 0.1 | SUS304-W1 | 0.1 | PU-based Elsstomer + PA | PU-based Elsstomer | B | C |
| Comp. Ex. 3 | SUS304-W1 | 0.1 | SUS304-W1 | 0.1 | PVDF + PCTFE | PVDF | B | C |

D: Poor resilience; not suitable for use as a flexible tube for an endoscope

The results of the resilience test are shown in the following Tables 1 and 2.

<2.2> Durability Test

A durability test was conducted on each of the flexible tubes of Examples 1–16 and Comparative Examples 1–3.

In the durability test, both ends of each of the flexible tubes were supported, and a 180° bending operation was repeated 400 times, whereafter the same resilience test described above was carried out to compare the resilience As is clear from Tables 1 and 2, all of the flexible tubes had good resilience.

Further, the flexible tubes of Examples 1–16 also had excellent durability. In particular, even though the outer cover of the flexible tube of each of Examples 11–16 had an average thickness (that is, the total of the average thicknesses of each of the three layers) that was thinner than that for Examples 1–10, the durability was roughly the same.

As described above, in the present invention, since the first fine wire having the coating layer is made more flexible that the second fine wire having no coating layer, adhesion (bonding strength) between the fine wire assembly (reticular tube) and the outer cover is improved, thereby enabling to prevent peeling-off of the outer cover from being caused when bending or twisting is applied to the flexible tube. Therefore, it is possible to provide a flexible tube for an endoscope having excellent resilience and durability.

Further, by appropriately selecting the constituent material of the coating layer and the constituent material of the outer cover as well as the properties resulted from the constituent materials, the above effect can be obtained more conspicuously.

Furthermore, in the present invention, the difference in the flexibilities between first fine wire and the second fine wire can be obtained reliably and relatively easily by such ways (methods) that (1) the first fine wire is made from a constituent material softer than a constituent material of the second fine wires, (2) the diameter of the first fine wire is made to be smaller than the diameter of the second fine wire, and (3) the processing condition and/or the heat treatment condition is changed in each of the first fine wire and the second fine wire, and thus manufacturing thereof can be made easily.

Moreover, in the case where the outer cover is formed into a laminated structure formed by laminating a plurality of layers, it is possible to obtain sufficient resilience and durability with an outer cover having a thinner thickness than that used in the case of a single layer outer cover. Accordingly, the provision of such laminated outer cover makes it possible to reduce the diameter of the flexible tube for an endoscope. Further, by selecting the proper material and thickness for each layer and combining these layers appropriately, it is possible to obtain an additional synergistic effect by the provisions of these layers. With this result, it becomes possible to obtain a flexible tube for an endoscope having excellent properties.

Finally, it is to be understood that many changes and additions may be made to the embodiments described above without departing from the scope and spirit of the invention as defined in the following claims.

Further, it is also to be understood that the present disclosure relates to subject matter contained in Japanese Patent Application No. 2002-146877 (filed on May 21, 2002) which is expressly incorporated herein by reference in its entirety.

What is claimed is:

1. A flexible tube for an endoscope, comprising:
a spiral tube comprising a helically wound band-shaped member;
a fine wire assembly comprising a plurality of fine wires and provided over the spiral tube; and
a flexible outer cover provided over the fine wire assembly
wherein the fine wires include at least one first fine wire and at least one second fine wire adjacent to the first fine wire, the first fine wire having a coating layer mainly of a resin material for providing enhanced adhesion with the outer cover and at least one second fine wire not having a coating layer, the first fine wire being more flexible than the second fine wire.

2. The flexible tube for an endoscope as claimed in claim 1, wherein the fine wire assembly includes a braiding of the first and second fine wires.

3. The flexible tube for an endoscope as claimed in claim 1, wherein the outer cover has a portion which is located adjacent to the fine wire assembly and comprises a constituent material, and the resin material of the coating layer contains the constituent material of the portion of the outer cover.

4. The flexible tube for an endoscope as claimed in claim 3, wherein the resin material of the coating layer contains the constituent material of the portion of the outer cover in an amount of 5 to 80 wt % of the resin material of the coating layer.

5. The flexible tube for an endoscope as claimed in claim 1, wherein the first fine wire comprises a material softer than a material of the second fine wire.

6. The flexible tube for an endoscope as claimed in claim 1, wherein the first fine wire has a diameter smaller than a diameter of the second fine wire.

7. The flexible tube for an endoscope as claimed in claim 1, wherein one of a processing condition and or a heat treatment condition of the first and second fine wires is different.

8. The flexible tube for an endoscope as claimed in claim 1, wherein the ratio of the number of the first fine wires to the number of the second fine wires in the fine wire assembly lies within the range of 1:15 to 3:1.

9. The flexible tube for an endoscope as claimed in claim 1, wherein the constituent material of the coating layer has a melting point higher than a melting point of the constituent material of the outer cover.

10. The flexible tube for an endoscope as claimed in claim 9, wherein the difference between the melting point of the constituent material of the coating layer and the melting point of the constituent material of the portion of the outer cover lies within the range of 4 to 200° C.

11. The flexible tube for an endoscope as claimed in claim 1, wherein the constituent material of the outer cover contains a polyurethane based elastomer.

12. The flexible tube for an endoscope as claimed in claim 1, wherein the constituent material of the coating layer contains a polyurethane based elastomer.

13. The flexible tube for an endoscope as claimed in claim 1, wherein the constituent material of the coating layer contains a polyamide based resin.

14. The flexible tube for an endoscope as claimed in claim 1, wherein the constituent material of the coating layer contains a fluoro based resin.

15. The flexible tube for an endoscope as claimed in claim 1, wherein the average thickness of the coating layer lies within the range of 0.01 to 0.1 mm.

16. The flexible tube for an endoscope as claimed in claim 1, wherein the average thickness of the outer cover lies within the range of 0.01 to 1.5 mm.

17. The flexible tube for an endoscope as claimed in claim 1, wherein the outer cover comprises a plurality of layers.

18. The flexible tube for an endoscope as claimed in claim 1, wherein the outer cover is formed by extrusion molding.

19. An endoscope including a flexible tube, the flexible tube comprising
a spiral tube comprising a helically wound band-shaped member;
a fine wire assembly comprising a plurality of fine wires and provided over the spiral tube; and
a flexible outer cover provided over the fine wire assembly
wherein the fine wires include at least one first fine wire and at least one second fine wire adjacent to the first fine wire, the first fine wire having a coating layer mainly of a resin material for providing enhanced adhesion with the outer cover and at least one second fine wire not having a coating layer, the first fine wire being more flexible than the second fine wire.

20. The flexible tube for an endoscope as claimed in claim 17, wherein each of the plurality of layers has a flexibility different than a flexibility of another of the plurality of layers.

21. An endoscope including a flexible tube, the flexible tube comprising
   a spiral tube comprising a helically wound band-shaped member;
   a fine wire assembly comprising a plurality of fine wires and provided over the spiral tube; and
   a flexible outer cover provided over the fine wire assembly
   wherein the fine wires include at least one first fine wire and at least one second fine wire adjacent to the first fine wire, the first fine wire having a coating layer mainly of a resin material and at least one second fine wire not having a coating layer, the first fine wire being more flexible than the second fine wire.

* * * * *